(12) United States Patent
Chen (10) Patent No.: US 10,816,677 B2
(45) Date of Patent: Oct. 27, 2020

(54) METHOD AND APPARATUS FOR POSITRON EMISSION TOMOGRAPHY

(71) Applicant: SHANGHAI UNITED IMAGING HEALTHCARE CO., LTD., Shanghai (CN)

(72) Inventor: Ze Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/422,499

(22) Filed: May 24, 2019

(65) Prior Publication Data
US 2019/0277978 A1 Sep. 12, 2019

Related U.S. Application Data

(63) Continuation of application No. 15/809,994, filed on Nov. 10, 2017, now Pat. No. 10,302,771, which is a (Continued)

(51) Int. Cl.
*G01T 1/161* (2006.01)
*G01T 1/29* (2006.01)
(Continued)

(52) U.S. Cl.
CPC ............ *G01T 1/1612* (2013.01); *A61B 6/037* (2013.01); *A61B 6/4417* (2013.01);
(Continued)

(58) Field of Classification Search
CPC ... G01T 1/1612; G01T 1/2985; G01T 1/1644; G01T 1/2002; G01T 1/2006;
(Continued)

(56) References Cited

U.S. PATENT DOCUMENTS 4,075,527 A 2/1978 Cummings
5,122,667 A * 6/1992 Thompson .............. G01T 1/202
250/363.01

(Continued)

FOREIGN PATENT DOCUMENTS

CN 101644780 A 2/2010
CN 102426380 A 4/2012
(Continued)

OTHER PUBLICATIONS

International Search Report in PCT/CN2017/098359 dated May 21, 2018, 6 pages.

(Continued)

*Primary Examiner* — Michael C Bryant
(74) *Attorney, Agent, or Firm* — Metis IP LLC (57) ABSTRACT

A PET detecting module may include a scintillator array configured to receive a radiation ray and generate optical signals in response to the received radiation ray. The scintillator array may have a plurality of rows of scintillators arranged in a first direction and a plurality of columns of scintillators arranged in a second direction. A first group of light guides may be arranged on a top surface of the scintillator array along the first direction. The light guide count of the first group of light guides may be less than the row count of the plurality of rows of scintillators. A second group of light guides may be arranged on a bottom surface of the scintillator array. The light guide count of the second group of light guides may be less than the column count of the plurality of columns of scintillators.

15 Claims, 7 Drawing Sheets

Related U.S. Application Data continuation of application No. PCT/CN2017/098359, filed on Aug. 21, 2017.

(51) Int. Cl.
| | |
|---|---|
| *G01T 1/164* | (2006.01) |
| *G01N 23/046* | (2018.01) |
| *A61B 6/00* | (2006.01) |
| *G01T 1/20* | (2006.01) |
| *A61B 6/03* | (2006.01) |

(52) U.S. Cl.
CPC ......... *G01N 23/046* (2013.01); *G01T 1/1644* (2013.01); *G01T 1/2002* (2013.01); *G01T 1/2006* (2013.01); *G01T 1/2985* (2013.01); *A61B 6/4241* (2013.01); *A61B 6/5205* (2013.01)

(58) Field of Classification Search
CPC .... G01N 23/046; A61B 6/4417; A61B 6/037; A61B 6/4241; A61B 6/5205; A61B 6/4266; A61B 6/52; A61B 6/44
See application file for complete search history.

(56) References Cited

U.S. PATENT DOCUMENTS

| | | | |
|---|---|---|---|
| 6,407,392 B1 * | 6/2002 | Tsuyuki | G01T 1/2018 250/366 |
| 7,385,201 B1 * | 6/2008 | Joung | G01T 1/2018 250/370.01 |
| 7,884,331 B2 | 2/2011 | Majewski et al. | |
| 8,467,644 B1 | 6/2013 | Kim et al. | |
| 8,822,931 B2 | 9/2014 | Laurence et al. | |
| 9,223,033 B2 | 12/2015 | Perna | |
| 9,575,192 B1 * | 2/2017 | Ng | G01T 1/20 |
| 9,841,510 B2 | 12/2017 | Simon et al. | |
| 2007/0272874 A1 | 11/2007 | Grodzins | |
| 2009/0134335 A1 | 5/2009 | Tsuda et al. | |
| 2011/0266450 A1 | 11/2011 | Majewski et al. | |
| 2013/0153776 A1 * | 6/2013 | Wieczorek | G01T 1/2018 250/366 |
| 2014/0231655 A1 | 8/2014 | Dueppenbecker et al. | |
| 2018/0136344 A1 | 5/2018 | Nelson et al. | |
| 2019/0056513 A1 * | 2/2019 | Chen | G01N 23/046 |
| 2019/0277978 A1 | 9/2019 | Chen | |

FOREIGN PATENT DOCUMENTS

| | | |
|---|---|---|
| CN | 102455431 A | 5/2012 |
| CN | 103376461 A | 10/2013 |
| CN | 105395208 A | 3/2016 |
| JP | 2005091334 A | 4/2005 |

OTHER PUBLICATIONS

Written Opinion in PCT/CN2017/098359 dated May, 21 2018, 4 pages.
First Office Action in Chinese Application No. 201710959034.7 dated Mar. 19, 2020, 12 pages.
First Office Action in Chinese Application No. 201710958789.5 dated Mar. 23, 2020, 21 pages.

* cited by examiner

METHOD AND APPARATUS FOR POSITRON EMISSION TOMOGRAPHY

CROSS-REFERENCE TO RELATED APPLICATIONS

This application is a continuation of U.S. patent application Ser. No. 15/809,994, filed Nov. 10, 2017, which claims priority of PCT Application No. PCT/CN2017/098359, filed Aug. 21, 2017, the contents of each of which are incorporated herein by reference.

TECHNICAL FIELD

The present disclosure generally relates to positron emission tomography (PET), and more specifically, relates to a method and apparatus for PET.

BACKGROUND

PET is a functional imaging technique in nuclear medicine that produces a three-dimensional image of functional processes in a living object. Typically, a short-lived radioactive isotope tracer, such as fluorodeoxyglucose (FDG), may be injected into the object. The tracer may undergo a positron emission decay (also known as the beta decay) and emit a positron. The positron may annihilate with an electron, generating a pair of annihilation photons (or gamma photons) that move in approximately opposite directions.

A PET system may include a PET detecting module to detect gamma rays. A PET detecting module may include a scintillator array and a plurality of optical channels (e.g., light guides). Each of the plurality of optical channels may guide a light signal to a photosensor. The optical channels may have various configurations. Each of plurality of optical channels may couple to a scintillator. An optical channel may couple to a row (or a column) of scintillators. Generally, with less optical channels, the cost and complexity of the PET system may be lower, but the detection performance of the PET system may be worse. It is desirable to seek a balance between maintaining a good performance and reducing the cost and complexity of the PET system.

SUMMARY

According to a first aspect of the present disclosure, a PET detecting module for detecting a radiation ray is provided. The PET detecting module may include a scintillator array, a first group of light guides and a second group of light guides. The scintillator array may be configured to receive a radiation ray and generate optical signals in response to the received radiation ray. The scintillator array may have a plurality of rows of scintillators arranged in a first direction and a plurality of columns of scintillators arranged in a second direction. The second direction may be approximately orthogonal to the first direction. The first group of light guides may be arranged on a top surface of the scintillator array along the first direction. The light guide count of the first group of light guides may be less than the row count of the plurality of rows of scintillators. The second group of light guides may be arranged on a bottom surface of the scintillator array along the second direction. The light guide count of the second group of light guides may be less than the column count of the plurality of columns of scintillators.

In some embodiments, at least one of the first group of light guides may be coupled to two adjacent rows of the plurality of rows of scintillators in the first direction. At least one of the second group of light guides may be coupled to two adjacent columns of the plurality of columns of scintillators in the second direction.

In some embodiments, the first group of light guides may extend in the first direction and distribute along the second direction. The second group of light guides may extend in the second direction and distribute along the first direction.

In some embodiments, a width of at least one of the first group of light guides may be less than a width of two adjacent rows of scintillators of the plurality of rows of scintillators. A width of at least one of the second group of light guides may be less than a width of two adjacent columns of scintillators of the plurality of rows of scintillators.

In some embodiments, the light guide count of the first group of light guides may be no less than a half of the row count of the plurality of rows of scintillators in the first direction. The light guide count of the second group of light guides may be no less than a half of the column count of the plurality of columns of scintillators in the second direction.

In some embodiments, the row count of the plurality of rows of scintillators in the first direction may equal the column count of the plurality of columns of scintillators in the second direction.

In some embodiments, the row count of the plurality of rows of scintillators in the first direction may be not equal to the column count of the plurality of columns of scintillators in the second direction.

In some embodiments, the first group of light guides may be physically connected to at least a portion of the top surface of the scintillator array. The second group of light guides may be physically connected to at least a portion of the bottom surface of the scintillator array.

In some embodiments, the first group of light guides may be coupled to a portion of the plurality of rows of scintillators in the first direction. The second group of light guides may be coupled to a portion of the plurality of columns of scintillators in the second direction.

In some embodiments, each of the first group of light guides may be coupled to at least one of the portion of the plurality of rows of scintillators in the first direction. Each of the second group of light guides may be coupled to at least one of the portion of the plurality of columns of scintillators in the second direction.

According to a second aspect of the present disclosure, a PET system is provided. The PET system may include a detector and at least one processor. The detector may be configured to receive radiation rays. The detector may include a detecting module. The detecting module may include a scintillator array, a first group of light guides and a second group of light guides. The scintillator array may be configured to receive a radiation ray and generate optical signals in response to the received radiation ray. The scintillator array may have a plurality of rows of scintillators arranged in a first direction and a plurality of columns of scintillators arranged in a second direction. The second direction may be approximately orthogonal to the first direction. The first group of light guides may be arranged on a top surface of the scintillator array. The second group of light guides may be arranged on a bottom surface of the scintillator array. The at least one processor may be configured to cause the system to: determine an intensity of an output from the first group of light guides according to the optical signals; determine an intensity of an output from the second group of light guides according to the optical signals; and identify, within the scintillator array, a scintillator that has interaction with the received radiation ray based on an intensity of the output from the first group of light guides and an intensity of the output from the second group of light guides.

In some embodiments, the first group of light guides may be arranged on a top surface of the scintillator array along the first direction. The second group of light guides may be arranged on a bottom surface of the scintillator array along the second direction. The light guide count of the first group of light guides may be less than the row count of the plurality of rows of scintillators, the light guide count of the second group of light guides may be less than the column count of the plurality of columns of scintillators.

In some embodiments, at least one of the first group of light guides may be coupled to two adjacent rows of the plurality of rows of scintillators in the first direction. At least one of the second group of light guides may be coupled to two adjacent columns of the plurality of columns of scintillators in the second direction.

In some embodiments, the system may further comprises one or more photosensors configured to convert the output from the first group of light guides and the output from the second group of light guides into electrical signals. The at least one processor may be configured to cause the PET system to: determine the intensity of the output from the first group of light guides and the intensity of the output from the second group of light guides according to the converted electrical signals.

In some embodiments, the one or more photosensors may include at least one silicon photomultiplier (SiPM).

In some embodiments, the at least one processor may be configured to cause the PET system to: determine a row number of the scintillator based on the intensity of the output from the first group of light guides; determine a column number of the scintillator based on the intensity of the output from the second group of light guides; and identify the scintillator based on the determined row number and the column number.

In some embodiments, the at least one processor may be configured to cause the PET system to determine a depth of the interaction with the received radiation ray in the identified scintillator based on the intensity of the output from the first group of light guides and the intensity of the output from the second group of light guides.

In some embodiments, the at least one processor may be configured to cause the PET system to reconstruct an image based, at least in part, on the row number of the identified scintillator, the column number of the identified scintillator, and the depth of the interaction with the received radiation ray in the identified scintillator.

In some embodiments, the at least one processor may be configured to cause the PET system to: detect an output component from each of the first group of light guides; determine an intensity component for each of the output components from the first group of light guides; and determine the intensity of the output from the first group of light guides according to the determined intensity components of the output components from the first group of light guides.

In some embodiments, the at least one processor may be configured to cause the PET system to: detect an output component from each of the second group of light guides; determine an intensity component for each of the output components from the second group of light guides; and determine the intensity of the output from the second group of light guides according to the determined intensity components of the output components from the second group of light guides.

According to a third aspect of the present disclosure, a method is provided. The method may be implemented on a computing device. The computing device may include at least one processor. The method may include one or more of the following operations. An intensity of an output from a first group of light guides of a scintillator array may be determined by the at least one processor according to optical signals generated by the scintillator in response to a received radiation ray. The first group of light guides may be arranged on a top surface of the scintillator array along a first direction. The scintillator array may have a plurality of rows of scintillators arranged in the first direction, a plurality of columns of scintillators arranged in a second direction. The second direction may be approximately orthogonal to the first direction. An intensity of an output from a second group of light guides of the scintillator array may be determined by the at least one processor according to the optical signals. The second group of light guides may be arranged on a bottom surface of the scintillator array along the second direction. A scintillator, within the scintillator array, that has interaction with the received radiation ray may be identified by the at least one processor based on the intensity of the output from the first group of light guides and the intensity of the output from the second group of light guides. The light guide count of the first group of light guides may be less than the row count of the plurality of rows of scintillators, the light guide count of the second group of light guides may be less than the column count of the plurality of columns of scintillators.

In some embodiment, at least one of the first group of light guides may be coupled to two adjacent rows of the plurality of rows of scintillators in the first direction. At least one of the second group of light guides may be coupled to two adjacent columns of the plurality of columns of scintillators in the second direction.

In some embodiments, electrical signals from one or more photosensors may be received. The electrical signals may be generated by the one or more photosensors by converting the output from the first group of light guides into the electrical signals. The intensity of the output from the first group of light guides may be determined according to the electrical signals.

In some embodiments, a row number of the scintillator may be determined based on the intensity of the output from the first group of light guides. A column number of the scintillator may be determined based on the intensity of the output from the second group of light guides. The scintillator may be identified based on the determined row number and the column number.

In some embodiments, a depth of the interaction with the received radiation ray in the identified scintillator may be determined.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 1:
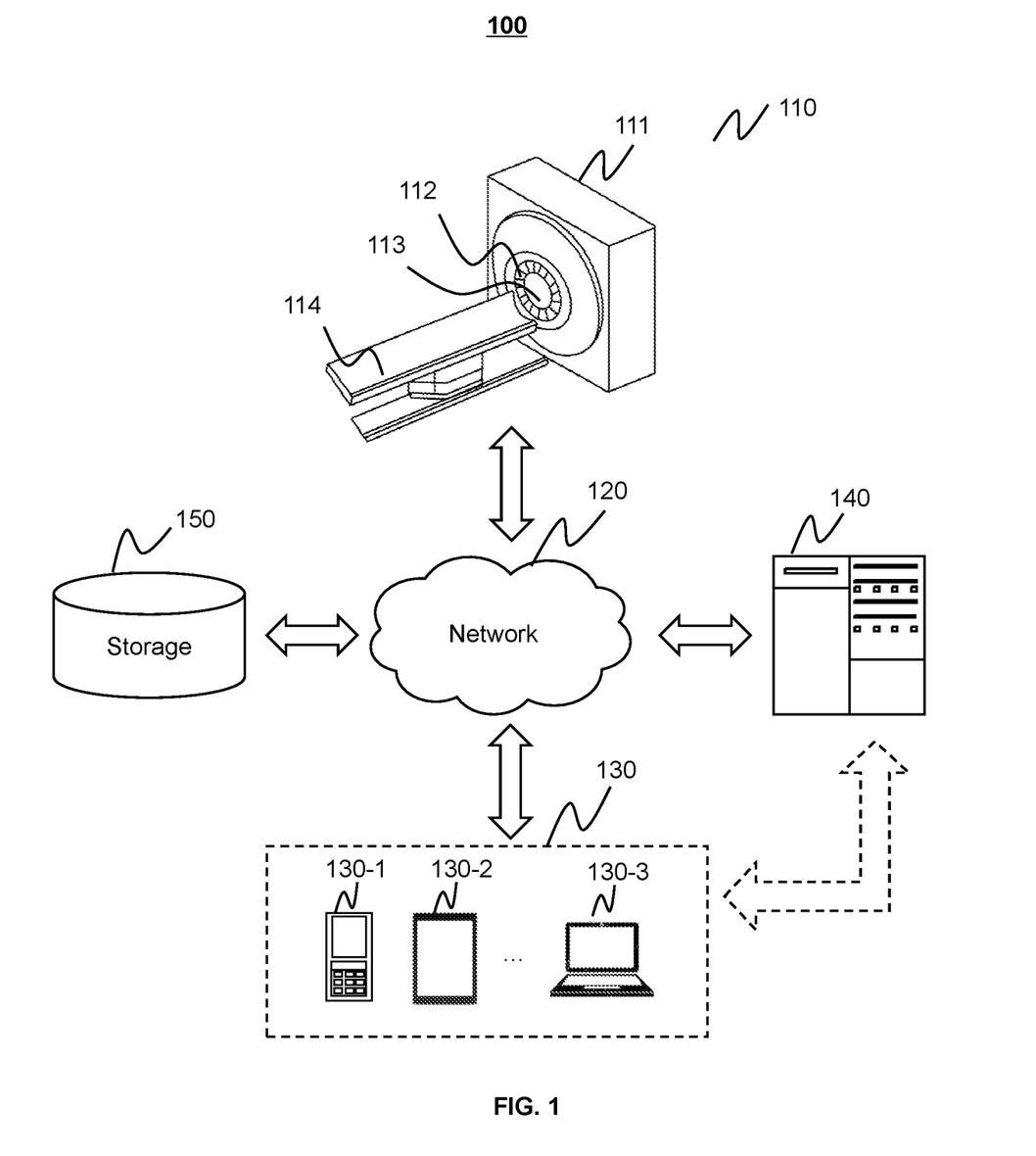
FIG. 1 is a schematic diagram illustrating an exemplary PET system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on a computing device (via, for example, computing device 140 as illustrated in FIG. 1) may be provided on a non-transitory computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

FIG. 1 is a schematic diagram illustrating an exemplary imaging system 100 according to some embodiments of the present disclosure. In some embodiments, the imaging system 100 may be a single-modal system, such as positron emission tomography (PET) imaging system. Alternatively, the imaging system 100 may be a multi-modal system, such as a positron emission tomography PET-CT imaging system, a PET-MRI imaging system, etc.

In some embodiments, the imaging system 100 may include a scanner 110, a network 120, one or more terminals 130, a computing device 140, and a storage 150. In some embodiments, the components of the imaging system 100 may be connected to each other via the network 120. Alternatively or additionally, the components of the imaging system 100 may be directly connected to each other.

The scanner 110 may scan an object and generate scanning data corresponding to the object. The object may include but is not limited to one or more organs, one or more types of tissues, or the like, of a patient. In some embodiments, the scanner 110 may be a medical scanning device, for example, a PET device, a PET-CT device, a PET-MRI device, etc. The scanner 110 may include a gantry 111, a detector 112, a scanning area 113, and a table 114. An object may be placed on the table 114. The table 114 may deliver the object to a target location in the scanning area 113. The detector 112 may detect radiation rays (e.g., gamma photons) emitted from the object in the scanning area 113. In some embodiments, the detector 112 may include a plurality of detection modules. The detection modules may be arranged in a suitable configuration, including but not limited to a ring (e.g., a detector ring), a rectangle, a triangle, or an array. Each of the plurality of detection modules may include a scintillator array, a first group of light guides, and a second group of light guides.

In application, a tracer (e.g., a radioactive isotope) may be injected into an object (via, for example, blood vessels of a patient). The atoms of the tracer may be converted into biologically active molecules. The molecules may gather in tissue of the patient. When a sufficient amount of the molecules are estimated to be gathered in the tissue (usually in an hour), the patient may be positioned on the table 114. The radioactive isotope may undergo a positron emission decay (i.e., the beta decay) and emits positrons. The positrons may interact with electrons inside the tissue (the interaction between positrons and electrons is called annihilation). The annihilations of the electrons and positrons may each produce a pair of annihilation photons (also referred to as gamma photons) that move in approximately opposite directions.

The gamma photons may be detected by the detector 112, and an image may be generated by the computing device 140 based on the information associated with the gamma photons. For example, the computing device 140 may determine the time-of-flight (time information) associated with each of the pairs of gamma photons. The computing device 140 may also determine the location where the annihilation happens based on the time-of-flight. After obtaining a plurality of locations of annihilations, the computing device 140 may generate a projection image (also referred to as a sonogram) based on the locations of the annihilations. The computing device 140 may reconstruct images based on the projection image and reconstruction techniques such as filtered back projection (FBP). The reconstructed images may indicate the tissue that contains a large number of biologically active molecules of the tracer. In some embodiments, the number of molecules of the tracer in a region may be related to biological functions of the tissues in the region. For example, if fluorodeoxyglucose (FDG) is used as the tracer in a PET scan, the number of tracer molecules in a region may be proportional to the rate of metabolism of glucose in the region. As tumors generally consume a huge amount of glucose, the region with a large number of molecules may be identified in a reconstructed image as tumor tissue.

The network 120 may include any suitable network that can facilitate the exchange of information and/or data between the components of the imaging system 100. In some embodiments, one or more components of the imaging system 100 (e.g., the scanner 110, the terminal 130, the computing device 140, the storage 150, etc.) may communicate information and/or data with one or more other components of the imaging system 100 via the network 120. For example, the computing device 140 may obtain image data (e.g., time information, energy information) from the scanner 110 via the network 120. As another example, the computing device 140 may obtain user instructions from the terminal 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof.

The terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal 130 may be part of the computing device 140.

The computing device 140 may process data and/or information obtained from the scanner 110, the terminal(s) 130, and/or the storage 150. For example, the computing device 140 may process image data (including time information, energy information, etc.) and reconstruct an image based on the image data. In some embodiments, the computing device 140 may be a single server or a server group. The server group may be centralized or distributed. In some embodiments, the computing device 140 may be local or remote. For example, the computing device 140 may access information and/or data stored in the scanner 110, the terminal(s) 130, and/or the storage 150 via the network 120. As another example, the computing device 140 may be directly connected to the scanner 110, the terminal(s) 130 and/or the storage 150 to access stored information and/or data. In some embodiments, the computing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the computing device 140, or a portion of the computing device 140 may be integrated into the scanner 110.

The computing device 140 may include a processor, a storage module, an input/output (I/O) and a communication port. The processor may execute computer instructions (e.g., program code) and perform functions of the computing device 140 described herein. The computer instructions may include, for example, routines, programs, objects, components, data structures, procedures, modules, and functions, which perform particular functions described herein. The storage module may store data/information obtained from the scanner 110, the terminal 130, the storage 150, and/or any other component of the imaging system 100. In some embodiments, the storage module may include a mass storage, a removable storage, a volatile read-and-write memory, a read-only memory (ROM), or the like, or any combination thereof. The I/O may input and/or output signals, data, information, etc. In some embodiments, the I/O may enable a user interaction with the computing device 140. In some embodiments, the I/O may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. The communication port may be connected to a network (e.g., the network 120) to facilitate data communications. The communication port may establish connections between the computing device 140 and the scanner 110, the terminal 130, and/or the storage 150. The connection may be a wired connection, a wireless connection, any other communication connection that can enable data transmission and/or reception, and/or any combination of these connections.

The storage 150 may store data, instructions, and/or any other information. In some embodiments, the storage 150 may store data obtained from the terminal(s) 130 and/or the computing device 140. In some embodiments, the storage 150 may store data and/or instructions that the computing device 140 may execute or use to perform exemplary methods described in the present disclosure. In some embodiments, the storage 150 may store image data (e.g., time information, energy information) obtained from the scanner 110. In some embodiments, the storage 150 may include a mass storage, removable storage, a volatile read-and-write memory, a read-only memory (ROM), or the like, or any combination thereof. In some embodiments, the storage 150 may be connected to the network 120 to communicate with one or more other components of the imaging system 100 (e.g., the computing device 140, the terminal(s) 130, etc.). Alternatively or additionally, the storage 150 may be part of the computing device 140.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. Merely by way of example, some other components may be added into the imaging system 100, such as a patient positioning unit, data acquisition electronics, power supplies, and other devices or units. However, those variations and modifications do not depart from the scope of the present disclosure.

Figure 2:
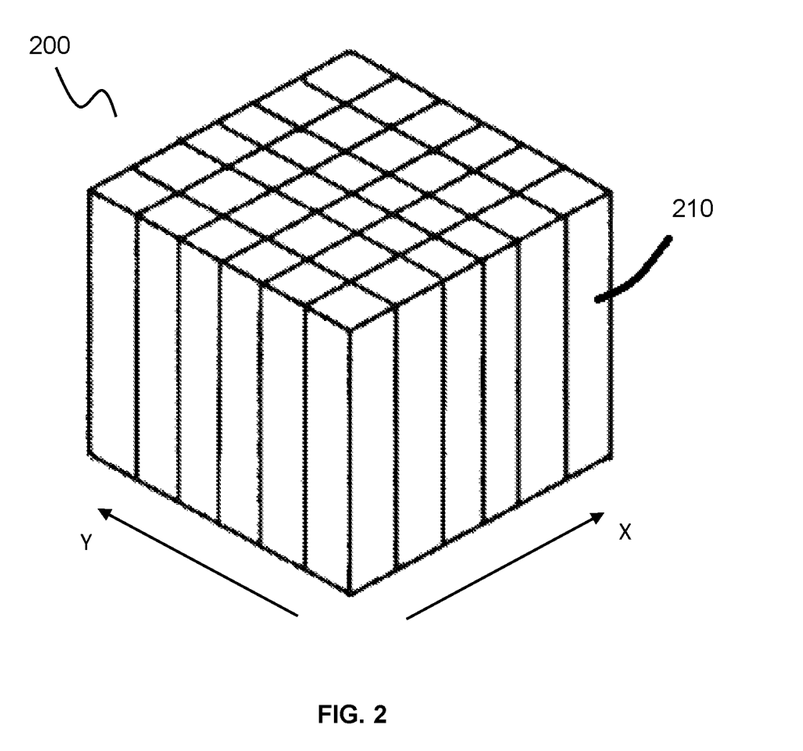
FIG. 2 is a schematic diagram illustrating an exemplary scintillator array according to some embodiments of the present disclosure.

FIG. 2 is a schematic diagram illustrating an exemplary scintillator array according to some embodiments of the present disclosure. As shown in FIG. 2, a scintillator array 200 may include a plurality of scintillators 210. The scintillators 210 may scintillate when a radiation ray (e.g., a gamma ray) photon collides the scintillator. The scintillators 210 may absorb the energy of the radiation ray photon and convert the absorbed energy into light signals.

In some embodiments, the scintillator array 200 may include a plurality of rows of scintillators (e.g., scintillators 210) arranged in a first direction (e.g., the direction of the X-axis) and a plurality of columns of scintillators arranged in a second direction (e.g., the direction of the Y-axis). The second direction may be approximately orthogonal to the first direction. In some embodiments, the row count of the rows of scintillators arranged in the X-axis direction (denoted as M) may equal the column count of the columns of scintillators arranged in the Y-axis direction (denoted as N). For example, both M and N may be in the range of 1 to 10.

Merely by way of example, both M and N may be 6. In some embodiments, M may be different from N. For example, the scintillator array 410 may have a configuration of 3*4, 4*6, 6*5, 3*3, 5*5 scintillators, or the like. In some embodiments, the scintillator array 410 may include only one scintillator.

In some embodiments, the scintillators 210 in the scintillator array 200 may be of the same size. Alternatively, at least two scintillators in the scintillator array 200 may be of different sizes. In some embodiments, a scintillator 210 may have a shape of a cuboid, a cube, a cylinder, or other suitable configuration.

In some embodiments, a scintillator 210 may be coated with (or have a coating of) an optical glue, a reflective material, or the like, on at least part of a side of the scintillator. The surface areas of scintillators may be coated with different coating materials.

In some embodiments, the scintillator array 200 may include two flat surfaces (e.g., a top surface of the scintillator array or a bottom surface of the scintillator array). The first group of light guides may be arranged on the top surface. The second group of light guides may be arranged on the bottom surface. In some embodiments, a scintillator 210 may include at least one material including, for example, bismuth germanium oxide (BGO), lutetium-yttrium oxyorthosilicate (LYSO), lutetium oxyorthosilicate (LSO), or the like.

Figure 3A:
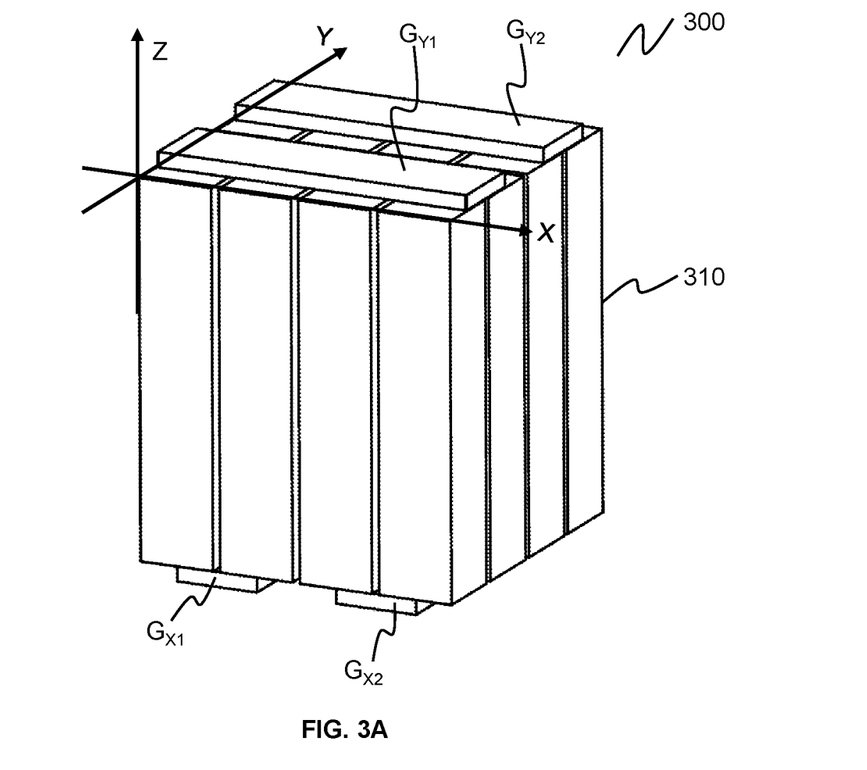
FIG. 3A is a schematic diagram illustrating an exemplary PET detecting module according to some embodiments of the present disclosure.

FIG. 3A is a schematic diagram illustrating an exemplary detecting module 300 according to some embodiments of the present disclosure. The detecting module 300 may include a 4×4 scintillator array 310 (which may be an embodiment of the scintillator array 200 illustrated in FIG. 2), the first group of light guides (e.g., light guide $G_{Y1}$ and $G_{Y2}$), and the second group of light guides (e.g., light guide $G_{X1}$ and $G_{X2}$). The first group of light guides may be arranged on the top surface of the 4×4 scintillator array 310 along the first direction (e.g., the direction of the X-axis). The second group of light guides may be arranged on the bottom surface of the 4×4 scintillator array 310 along the second direction (e.g., the direction of the Y-axis). In some embodiments, the light guide count of the first group of light guides may be less than the row count of the plurality of rows of scintillators. The light guide count of the second group of light guides may be less than the column count of the plurality of columns of scintillators.

In some embodiments, the first group of light guides may be physically (and/or directly) connected to at least a portion of the top surface of the scintillator array. For example, the first group of light guides may be coupled (i.e., optically coupled) to at least a portion of the top surface of the scintillator array. The second group of light guides may be physically (and/or directly) connected to at least a portion of the bottom surface of the scintillator array. In some embodiments, the first group of light guides may be coupled to a portion of the plurality of rows of scintillators in the first direction. The second group of light guides may be coupled to a portion of the plurality of columns of scintillators in the second direction. In some embodiments, each of the first group of light guides may be coupled to at least one of the portion of the plurality of rows of scintillators in the first direction. Each of the second group of light guides is coupled to at least one of the portion of the plurality of columns of scintillators in the second direction. More descriptions of the 4×4 scintillator array 310 may be found in FIG. 4 and the description thereof.

Figure 3B:
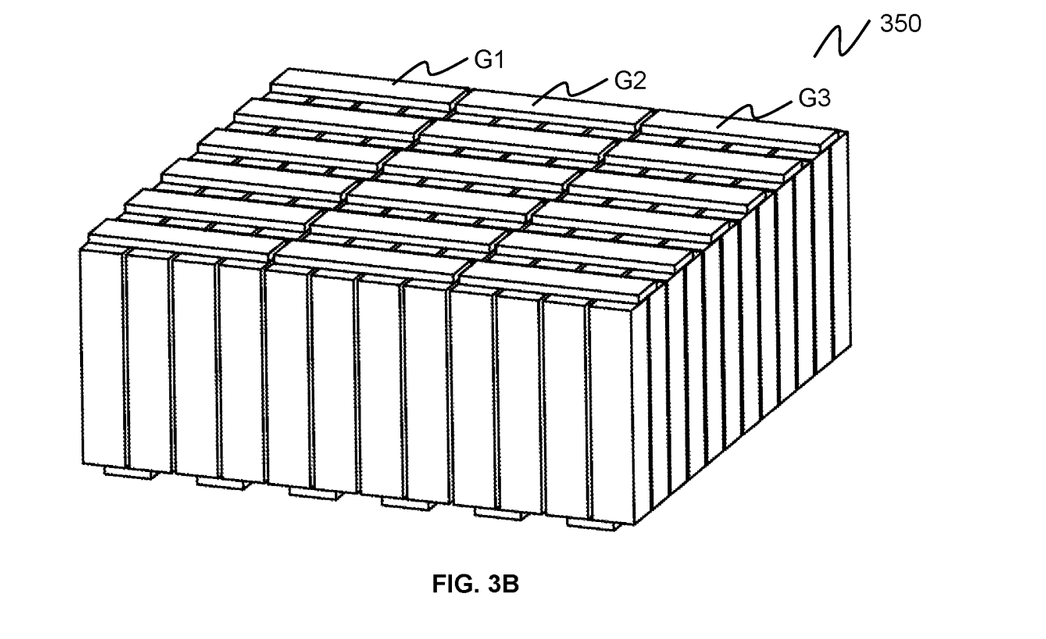
FIG. 3B is a schematic diagram illustrating a group of exemplary PET detecting modules according to some embodiments of the present disclosure.

FIG. 3B is a schematic diagram illustrating a group of exemplary PET detecting modules 350 according to some embodiments of the present disclosure. The group of detecting modules 350 may include one or more detecting modules 300 (illustrated in FIG. 3A). For example, the group of detecting modules 350 may include 9 (arranged as 3×3) detecting modules 300. Further, one or more groups of detecting modules 350 may constitute the detector 112. As illustrated in FIG. 3B, the group of detecting modules 350 may include a scintillator array (including 12×12 scintillators), with a 6×3 light guide array arranged on its top surface and a 3×6 light guide array arranged on its bottom surface. In some embodiments, the light guides in the same row (e.g., a light guide G1, a light guide G2, and a light guide G3) may be integrated into one light guide.

It should be noted that the row counts or column counts mentioned in FIGS. 3A and 3B, and the arrangement of the light guides are merely provided for the purpose of illustration, and not intended to limit the scope of the present disclosure. For example, the detecting module 300 may include 5×5 scintillators, 6×6 scintillators, 3×4 scintillators, etc. As another example, the group of detecting modules 350 may include 4×4 detecting modules 300, 5×5 detecting modules 300, 6×8 detecting modules 300, or the like.

Figure 4A:
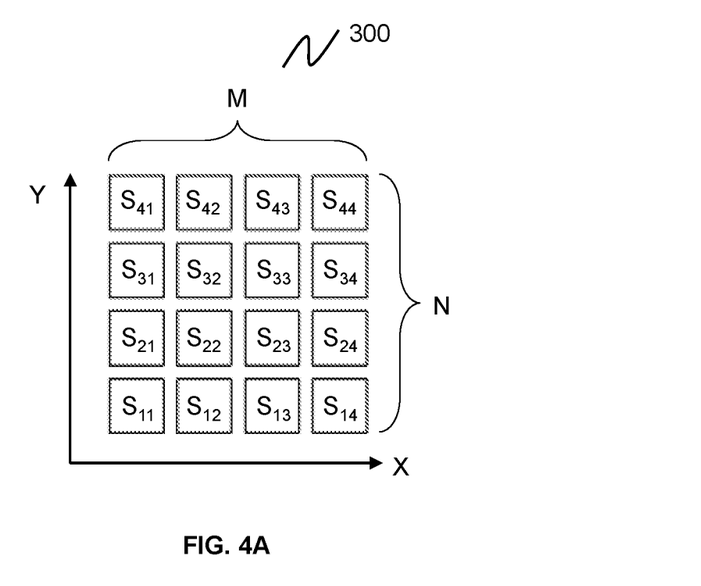
FIGS. 4A-4D illustrate various views of an exemplary detecting module according to some embodiments of the present disclosure.
Figure 4B:
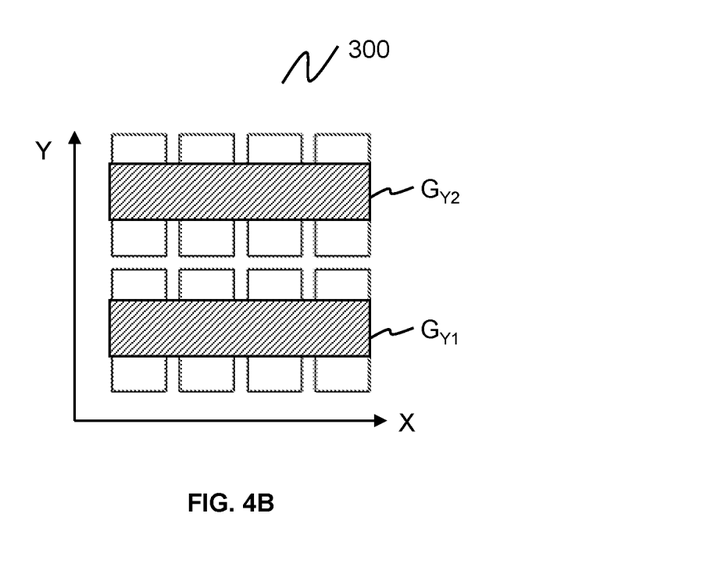

FIGS. 4A-4D illustrate various views of an exemplary detecting module according to some embodiments of the present disclosure. In some embodiments, a detecting module 300 may be configured to receive a radiation ray and generate optical signals in response to the received radiation ray. The optical signals may be light rays emitted when a radiation ray interacts with a scintillator. As shown in FIGS. 4A-4D, the detecting module 300 may include a scintillator array. The scintillator array may include a plurality of rows of scintillators arranged in a first direction (extending in the X-axis direction). The scintillator array may include a plurality of columns of scintillators arranged in a second direction (extending in the Y-axis direction). The second direction may be approximately orthogonal to the first direction. In some embodiments, the scintillator array may include a top surface and a bottom surface. The top surface and the bottom surface may be generally flat. The top surface or the bottom surface may face a detecting region of the PET system. In some embodiments, the first group of light guides may be arranged on a surface (e.g., the top surface) of the scintillator array. The light guides may be used to guide optical signals from the scintillators to a photosensor. In some embodiments, one of the first group of light guides may be coupled to two adjacent rows of the N rows of scintillators. The second group of light guides may be arranged on the opposite surface (e.g., the bottom surface) of the scintillator array. One of the second group of light guides may be coupled to two adjacent columns of the M columns of scintillators. In some embodiments, the first group of light guides may extend (i.e., prolongate) along the first direction and distribute in the second direction. The second group of light guides may extend along the second direction and distribute in the first direction. For example, as shown in FIG. 4B, two light guides, $G_{Y1}$ and $G_{Y2}$, may extend along the X-direction and distribute in the Y-direction.

In some embodiments, a width of one of the first group of light guides may be less than the total width of two adjacent rows of scintillators (i.e., the sum of the widths of two adjacent rows of scintillators). A width of one of the second group of light guides may be less than the total width of two adjacent columns of scintillators (i.e., the sum of the widths of two adjacent columns of scintillators). In some embodiments, the light guide count of the first group of light guides may be no less than a half of the row count of the plurality of rows of scintillators in the first direction. The light guide count of the second group of light guides may be no less than a half of the column count of the plurality of columns of scintillators in the second direction.

FIG. 4A illustrates the top view of the detecting module 300. In some embodiments, the row count of the plurality of rows of scintillators arranged in the X-direction (marked as N) may equal to the column count of the plurality of columns of scintillators arranged in the Y-direction (marked as M). For example, in the illustrated embodiment of FIG. 4A, N is 4, and M is 4. As another example, both N and M may equal 2, 3, 5, 6, or the like. Alternatively, N may not equal M. For example, a scintillator array with N rows and M columns (marked as N*M) of scintillators may be 3*4, 4*6, 6*5, or the like.

FIG. 4B illustrates the X-Y perspective view of the detecting module 300. As shown in FIG. 4B, the detecting module 300 may further include the first group of light guides (e.g., $G_{Y1}$, $G_{Y2}$) extending along the X-direction. The light guide ($G_{Y1}$ or $G_{Y2}$) may be coupled to two adjacent rows of scintillators. For example, the light guide $G_{Y1}$ may be coupled to the first row of the scintillators (e.g., $S_{11}$, $S_{12}$, $S_{13}$, and $S_{14}$) and the second row of the scintillators (e.g., $S_{21}$, $S_{22}$, $S_{23}$, and $S_{24}$). The light guide $G_{Y1}$ may accumulate light signals from any of the 8 scintillators of the first and second rows of the scintillators. In some embodiments, if N is an even number, the light guide count of the first group of light guides may be a half of N. For example, if N equals 6, the light guide count of the first group of light guides may be 3. Similarly, if M is an even number, the light guide count of the second group of light guides may be a half of M. In some embodiments, if N is an odd number, the light guide count of the first group of light guides may be a half of N+1. For example, if N equals 7, the light guide count of the first group of light guides may be 4. Similarly, if M is an odd number, the light guide count of the second group of light guides may be a half of M+1.

Figure 4C:
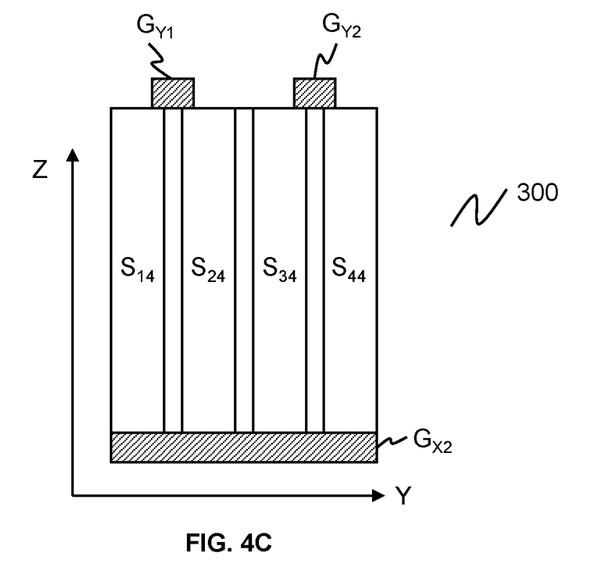
Figure 4D:
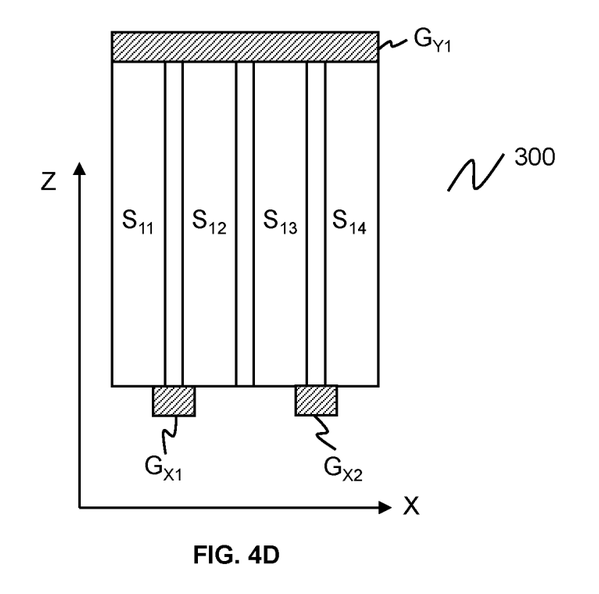

FIG. 4C shows a side view of the detecting module 300 seen in the Y-Z plane. Light guides $G_{Y1}$ and $G_{Y2}$ may be arranged on the top surface of the scintillator array. The light guide $G_{X2}$ may be arranged on the bottom surface as well and coupled to the third column of the scintillators (including $S_{13}$, $S_{23}$, $S_{33}$ and $S_{43}$) and the fourth column of the scintillators (including $S_{14}$, $S_{24}$, $S_{34}$ and $S_{44}$). Although invisible in FIG. 4C, the light guide $G_{X1}$ may be arranged on the bottom surface. In this example, the light guides $G_{Y1}$ and $G_{Y2}$ may be orthogonal to the light guides $G_{Y1}$ and $G_{X2}$. FIG. 4D shows a side view of the detecting module 300 seen in the X-Z plane. The light guides $G_{Y1}$ and $G_{Y2}$ may be on the top surface (although only $G_{Y1}$ is visible in FIG. 4D). The light guides $G_{X1}$ and $G_{X2}$, which may be orthogonal to $G_{Y1}$ and $G_{Y2}$, may be arranged on the bottom surface.

In some embodiments, the computing device 140 may read the light guides, convert an output of the light guides into an electrical signal. The computing device 140 may identify which scintillator within the scintillator array may have a radiation ray (gamma ray) interaction, based on the electrical signals. The computing device 140 may further determine a depth of interaction of the received radiation ray in the identified scintillator. More details of the scintillator identification and the depth determination may be found in FIG. 6 and the relevant description.

Figure 5:
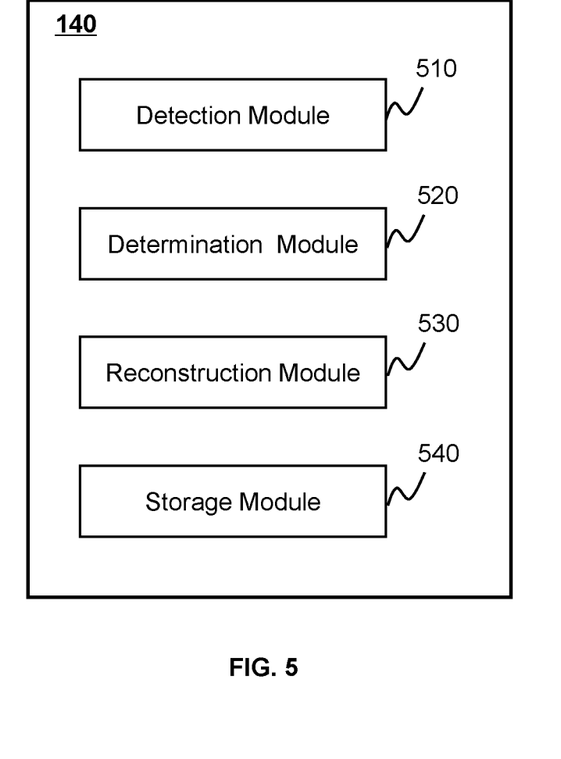
FIG. 5 is a block diagram illustrating an exemplary computing device according to some embodiments of the present disclosure.

FIG. 5 is a block diagram illustrating an exemplary computing device according to some embodiments of the present disclosure. As shown in FIG. 5, the computing device 140 may include a detection module 510, a determination module 520, a reconstruction module 530, and a storage module 540. The detection module 510, determination module 520, reconstruction module 530, and storage module 540 may refer to logic embodied in hardware or firmware, or to a collection of software instructions. The modules described herein may be implemented as software and/or hardware modules and may be stored in any type of non-transitory computer-readable medium or other storage device. In some embodiments, a software module may be compiled and linked into an executable program. It will be appreciated that software modules can be callable from other modules or from themselves, and/or can be invoked in response to detected events or interrupts. Software modules configured for execution on computing devices (e.g., a processor of computing device 140) can be provided on a computer readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in a firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules, but can be represented in hardware or firmware. In general, the modules described herein refer to logical modules that can be combined with other modules or divided into sub-modules despite their physical organization or storage.

The detection module 510 may be configured to detect an output from light guides. For example, the detection module 510 may be configured to detect an output from the first group of light guides and an output from the second group of light guides. In some embodiments, the output from the first group of light guides or an output from the second group of light guides may be an optical signal including optical signals collected from the scintillators to which a light guide is coupled.

The determination module 520 may be configured to identify, within the scintillator array, a scintillator that has a radiation ray interaction with a received radiation ray. In some embodiments, the determination module 520 may determine a depth of interaction of the received radiation ray in the identified scintillator. The detection module 520 may determine the intensity of the output from the first group of light guides. The detection module 520 may also determine the intensity of the output from the second group of light guides.

The reconstruction module 530 may be configured to reconstruct a PET image based on the identified scintillators and depths of interaction of the received radiation ray in the identified scintillator.

The storage module 540 may be configured to store PET data, control parameters, processed PET data, or the like, or any combination thereof. In some embodiments, the storage module 540 may store one or more scanning protocols and/or encoded PET data. In some embodiments, the storage module 540 may store one or more programs and/or instructions that may be executed by the computing device 140 to perform exemplary methods described in this disclosure.

In some embodiments, one or more modules illustrated in FIG. 5 may be implemented in at least a part of the exemplary PET system as illustrated in FIG. 1. For example, the acquisition module 510, the control module 520, the storage module 530, and/or the processing module 540 may be integrated into a console (not shown). Via the console, a user may set parameters for scanning an object, controlling imaging processes, controlling parameters for reconstruction of an image, viewing reconstructed images, etc. In some embodiments, the console may be implemented via the computing device 140 and/or the terminal 160.

Figure 6:
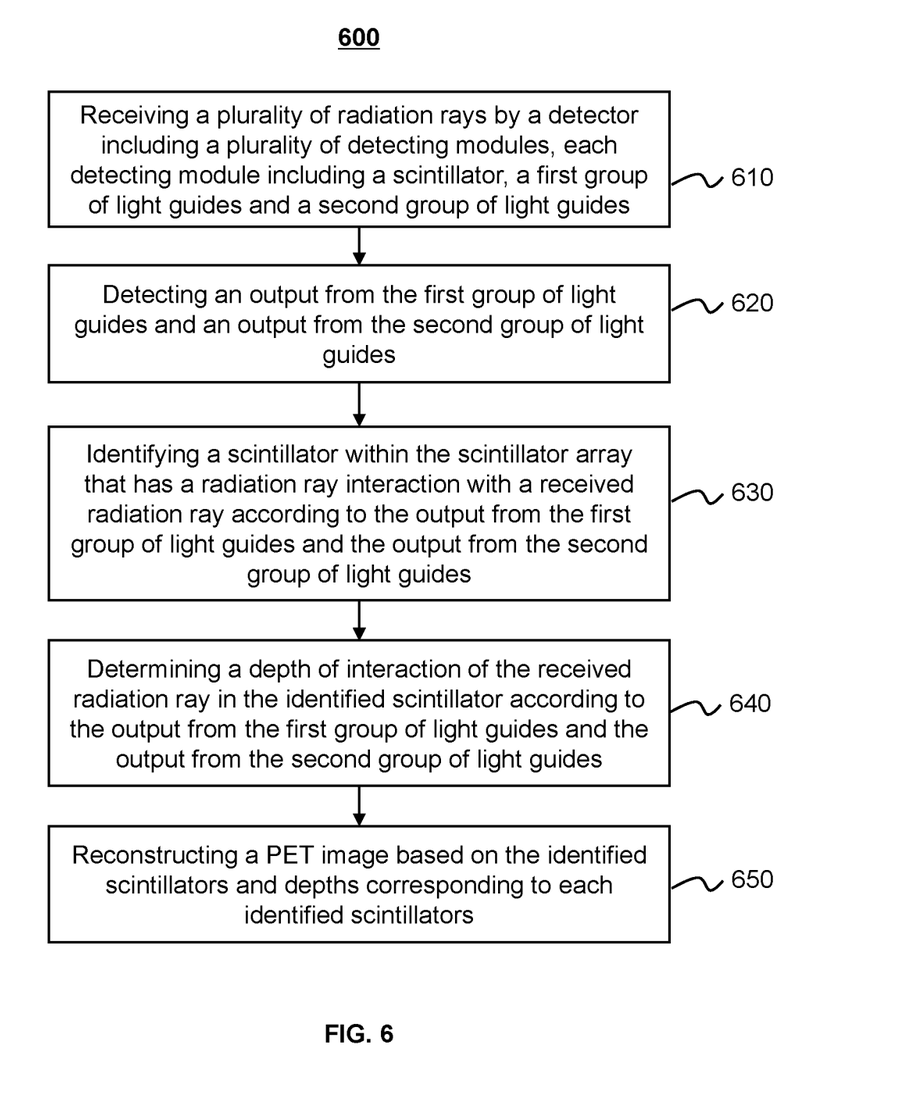
FIG. 6 is a flowchart illustrating an exemplary process for PET imaging according to some embodiments of the present disclosure.

FIG. 6 is a flowchart illustrating an exemplary process for PET imaging according to some embodiments of the present disclosure. In some embodiments, process 600 may be a process for reconstructing a PET image. The process 600 may be implemented by the computing device 140 and executed by a processor of the computing device 140.

In 610, a detector, including a plurality of detecting modules, may receive a plurality of radiation rays (gamma rays) that emitted from a subject. The plurality of detecting modules may be used to detect the radiation rays. Each of the plurality of detecting modules may include a scintillator array. Each of the plurality of detecting modules may include the first group of light guides and the second group of light guides. The scintillator array may have N rows of scintillators arranged in a first direction and M columns of scintillators arranged in a second direction. The second direction may be approximately orthogonal to the first direction. The detecting module may include the first group of light guides arranged on a top surface of the scintillator array and the second group of light guides arranged on a bottom surface of the scintillator array. In some embodiments, one light guide may be coupled to two adjacent rows of the plurality of rows of scintillators in the first direction. One light guide may be coupled to two adjacent columns of the plurality of columns of scintillators in the second direction. In some embodiments, N may equal M. For example, N=M=4.

In some embodiments, the width of one of the first group of light guides may be less than the total width of two adjacent rows of scintillators (i.e., the sum of the widths of two adjacent rows of scintillators), and the width of one of the second group of light guides may be less than the total width of two adjacent columns of scintillators (i.e., the sum of the widths of two adjacent columns of scintillators). In some embodiments, the width of each of the light guides may be a constant value. For example, the constant value may be the width of a scintillator. In some embodiments, the light guide count of the first group of light guides is no less than a half of N, and the light guide count of the second group of light guides is no less than a half of M. For example, when N=M=4, the light guide count of the first group of light guides may be 2, and the light guide count of the second group of light guides may be 2 as well.

In 620, for a scintillator array, the detection module 510 may detect an output from the first group of light guides and an output from the second group of light guides. In some embodiments, a light guide may be coupled to two adjacent rows (or two adjacent columns) of scintillators. For example, two adjacent rows (or two adjacent columns) of scintillators may include 8 scintillators (as described in FIGS. 4A-4D). The output from the light guide may be an optical signal including optical signals from the scintillators to which the light guide is coupled. In some embodiments, the optical signals may be generated by the scintillator array 300 in response to a received radiation ray.

In some embodiments, one or more photosensors, arranged in the detecting module 510, may be configured to convert the output from the first group of light guides and the second group of light guides into an electrical signal. The determination module 520 may determine the intensity of the output from the first group of light guides and the intensity of the output from the second group of light guides according to the electrical signal generated by the one or more photosensors.

In 630, the determination module 520 may identify, within the scintillator array, a scintillator that has a radiation ray interaction with a received radiation ray based on the intensity of the output from the first group of light guides and the intensity of the output from the second group of light guides. For illustration and referring to FIGS. 4A-4D, X1 may represent the intensity of the output from the light guide $G_{X1}$. X2 may represent the intensity of the output from the light guide $G_{X2}$. Y1 may represent the intensity of the output from the light guide $G_{Y1}$. Y2 may represent the intensity of the output from the light guide $G_{Y2}$. The location of the radiation ray interaction in the scintillator array may be determined according to equations (1) and (2):

$$X=X1/(X1+X2) \quad (1),$$

$$Y=Y1/(Y1+Y2) \quad (2),$$

where X1 represents the intensity of the output from the light guide $G_{X1}$, X2 represents the intensity of the output from the light guide $G_{X2}$, X represents a normalized location in the first direction of the radiation ray interaction, Y1 represents the intensity of the output from the light guide $G_{Y1}$, Y2 represents the intensity of the output from the light guide $G_{Y2}$, Y represents a normalized location in the second direction of the radiation ray interaction. The value of X may be used to determine which column of scintillators has radiation ray interaction. The value of Y may be used to determine which row of scintillators has radiation ray interaction. Take Y=Y1/(Y1+Y2) as an example. Three thresholds T1, T2, T3 may be designated for determining the scintillator(s) that has radiation ray interaction. If 0≤Y≤T1, the location of the radiation ray interaction may be determined in the fourth row of the scintillators (including $S_{41}$, $S_{42}$, $S_{43}$, and $S_{44}$). If T1<Y≤T2, the location of the radiation ray interaction may be determined in the third row of the scintillators (including $S_{31}$, $S_{32}$, $S_{33}$, and $S_{34}$). If T2<Y≤T3, the location of the radiation ray interaction may be determined in the second row of the scintillators (including $S_{21}$, $S_{22}$, $S_{23}$, and $S_{24}$). If T3<Y≤1, the location of the radiation ray interaction may be determined in the first row of the scintillators (including $S_{11}$, $S_{12}$, $S_{13}$, and $S_{14}$). In some embodiments, the three threshold T1, T2, and T3 may be designated according to different situations (e.g., different width of the light guide). For example, T1 may equal 0.3, T2 may equal 0.5, and T3 may equal 0.7. Similarly, which column of the scintillators has the radiation ray interaction may be determined based on X=X1/(X1+X2) and the three thresholds T1, T2, and T3. In some embodiments, if M and/or N not equal 4, the number of the thresholds may be changed accordingly. For example, if both M and N equal 6, five thresholds may be designated for determining the scintillator(s) that has radiation ray interaction.

In 640, the determination module 520 may determine a depth of interaction of the received radiation ray in the identified scintillator based on the intensity of the output from the first group of light guides and the intensity of the output from the second group of light guides. The depth of the radiation ray interaction in the scintillator array may be determined according to equation (3)

$$Z=(X1+X2)/(X1+X2+Y1+Y2) \quad (3),$$

where X1 represents the intensity of the output from the light guide $G_{X1}$, X2 represents the intensity of the output from the light guide $G_{X2}$, Y1 represents the intensity of the output from the light guide $G_{Y1}$, Y2 represents the intensity of the output from the light guide $G_{Y2}$, Z represents a normalized depth of the radiation ray interaction in the scintillator array. The value of Z may be in a range between 0 to 1. If Z is bigger than 0.5, the location of the interaction of the received radiation ray may be closer to the top surface. If Z is smaller than 0.5, the location of the interaction of the received radiation ray may be closer to the bottom surface.

In 650, the reconstruction module 530 may reconstruct a PET image based on the identified scintillators and depths corresponding to each identified scintillators. In some embodiments, the reconstruction module 530 may reconstruct the image based on reconstruction techniques such as filtered back projection (FBP). A reconstructed image may illustrate the tissue that contains a large number of biologically active molecules of the tracer.

It should be noted that the above description of the processing module is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the weighted synthesis operation may be unnecessary.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as JAVA, SCALA, SMALLTALK, EIFFEL, JADE, EMERALD, C++, C #, VB. NET, PYTHON or the like, conventional procedural programming languages, such as the "C" programming language, Visual Basic, Fortran 2013, PERL, COBOL 2012, PHP, ABAP, dynamic programming languages such as PYTHON, RUBY, and GROOVY, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximately," or "substantially." For example, "about," "approximately," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A PET system, comprising:
 a detector configured to receive radiation rays, the detector comprising a detecting module, the detecting module comprising:
  a scintillator array configured to receive a radiation ray and generate optical signals in response to the received radiation ray, the scintillator array including a plurality of rows of scintillators and a plurality of columns of scintillators;
  a first group of light guides arranged on a top surface of the scintillator array, wherein a count of the first group of light guides is equal to a row count of the plurality of rows of scintillators or is equal to a half of the row count; and
  a second group of light guides arranged on a bottom surface of the scintillator array, wherein a count of the second group of light guides is equal to a column count of the plurality of columns of scintillators or is equal to a half of the column count; and
 at least one processor configured to cause the PET system to:
  determine an intensity of an output from the first group of light guides according to the optical signals;
  determine an intensity of an output from the second group of light guides according to the optical signals; and determine a depth of the interaction with the received radiation ray in the scintillator array through dividing the intensity of the output from the second group of light guides by a sum of the intensity of the output from the second group of light guides and the intensity of the output from the first group of light guides.

2. The PET system of claim 1, wherein the at least one processor is further configured to cause the PET system to reconstruct an image based, at least in part, on the depth of the interaction with the received radiation ray in the scintillator array.

3. The PET system of claim 1, wherein the plurality of rows of scintillators are arranged in a first direction and the plurality of columns of scintillators are arranged in a second direction, the second direction being approximately orthogonal to the first direction.

4. The PET system of claim 3, wherein
the first group of light guides is arranged on the top surface of the scintillator array along the first direction; and
the second group of light guides is arranged on the bottom surface of the scintillator array along the second direction.

5. The PET system of claim 1, wherein
at least one of the first group of light guides is coupled to two adjacent rows of the plurality of rows of scintillators in the first direction, and
at least one of the second group of light guides is coupled to two adjacent columns of the plurality of columns of scintillators in the second direction.

6. The PET system of claim 1, wherein
the at least one processor is further configured to cause the PET system to identify, within the scintillator array, a scintillator that has interaction with the received radiation ray based on the intensity of the output from the first group of light guides and the intensity of the output from the second group of light guides.

7. The PET system of claim 6, wherein
the at least one processor is further configured to cause the PET system to determine a depth of the interaction with the received radiation ray in the identified scintillator based on the intensity of the output from the first group of light guides and the intensity of the output from the second group of light guides.

8. The PET system of claim 1, further comprising one or more photosensors configured to convert the output from the first group of light guides and the output from the second group of light guides into electrical signals, wherein
to determine a depth of the interaction with the received radiation ray in the identified scintillator, the at least one processor is further configured to cause the PET system to:
determine the intensity of the output from the first group of light guides and the intensity of the output from the second group of light guides according to the converted electrical signals.

9. A method implemented on a computing device, the computing device including at least one processor, the method comprising:
determining, by the at least one processor, an intensity of an output from a first group of light guides of a scintillator array according to optical signals generated by the scintillator in response to a received radiation ray, the first group of light guides being arranged on a top surface of the scintillator array, the scintillator array including a plurality of rows of scintillators and a plurality of columns of scintillators, a count of the first group of light guides being equal to a row count of the plurality of rows of scintillators or being equal to a half of the row count;
determining, by the at least one processor, an intensity of an output from a second group of light guides of the scintillator array according to the optical signals, the second group of light guides being arranged on a bottom surface of the scintillator array, a count of the second group of light guides being equal to a column count of the plurality of columns of scintillators or being equal to a half of the column count; and
determining, by the at least one processor, a depth of the interaction with the received radiation ray in the scintillator array through dividing the intensity of the output from the second group of light guides by a sum of the intensity of the output from the second group of light guides and the intensity of the output from the first group of light guides.

10. The method of claim 9, wherein determining the intensity of the output from the first group of light guides of the scintillator array according to the optical signals comprises:
receiving electrical signals from one or more photosensors, the electrical signals being generated by the one or more photosensors by converting the output from the first group of light guides into the electrical signals; and
determining the intensity of the output from the first group of light guides according to the electrical signals.

11. The method of claim 9, wherein the scintillator array includes a plurality of rows of scintillators are arranged in a first direction and the plurality of columns of scintillators are arranged in a second direction, the second direction being approximately orthogonal to the first direction.

12. The method of claim 11, wherein
the first group of light guides is arranged on the top surface of the scintillator array along the first direction; and
the second group of light guides is arranged on the bottom surface of the scintillator array along the second direction.

13. The method of claim 9, further comprising:
identifying, within the scintillator array, a scintillator that has interaction with the received radiation ray based on the intensity of the output from the first group of light guides and the intensity of the output from the second group of light guides.

14. The method of claim 13, wherein determining, by the at least one processor, a depth of the interaction with the received radiation ray in the scintillator array further comprising:
determining a depth of the interaction with the received radiation ray in the identified scintillator based on the intensity of the output from the first group of light guides and the intensity of the output from the second group of light guides.

15. A PET device comprising a detecting module for detecting a radiation ray and a determination module, wherein
the detecting module comprises:
a scintillator array configured to receive a radiation ray and generate optical signals in response to the received radiation ray, the scintillator array including a plurality of rows of scintillators and a plurality of columns of scintillators;
a first group of light guides arranged on a top surface of the scintillator array, a count of the first group of light guides being equal to a row count of the plurality of rows of scintillators or being equal to a half of the row count; and a second group of light guides arranged on a bottom surface of the scintillator array, a count of the second group of light guides being equal to a column count of the plurality of columns of scintillators or being equal to a half of the column count; and the determination module is configured to:

determine an intensity of an output from the first group of light guides according to the optical signals;

determine an intensity of an output from the second group of light guides according to the optical signals; and determine a depth of the interaction with the received radiation ray in the scintillator array through dividing the intensity of the output from the second group of light guides by a sum of the intensity of the output from the second group of light guides and the intensity of the output from the first group of light guides.

\* \* \* \* \*